United States Patent
Banerjee et al.

(10) Patent No.: US 11,566,251 B2
(45) Date of Patent: Jan. 31, 2023

(54) GENETICALLY MODIFIED ALGA, SEQUENCES AND METHODS THEREOF

(71) Applicant: Reliance Industries Limited, Mumbai (IN)

(72) Inventors: Arun Banerjee, Maharashtra (IN); Gautam Das, Telangana (IN); Sonal Santosh Patil, Maharashtra (IN); Sourav Sanyal, West Bengal (IN); Smita Dattatraya Patil, Maharashtra (IN); Santanu Dasgupta, Maharashtra (IN)

(73) Assignee: Reliance Industries Limited, Mumbai (IN)

( * ) Notice: Subject to any disclaimer, the term of this patent is extended or adjusted under 35 U.S.C. 154(b) by 413 days.

(21) Appl. No.: 16/700,557

(22) Filed: Dec. 2, 2019

(65) Prior Publication Data
US 2020/0172916 A1    Jun. 4, 2020

(30) Foreign Application Priority Data
Dec. 3, 2018   (IN) .............................. 201821045691

(51) Int. Cl.
*C12N 15/79* (2006.01)
*A01G 33/00* (2006.01)
*C12N 1/12* (2006.01)
*C07K 14/80* (2006.01)

(52) U.S. Cl.
CPC ............. *C12N 15/79* (2013.01); *A01G 33/00* (2013.01); *C07K 14/80* (2013.01); *C12N 1/12* (2013.01)

(58) Field of Classification Search
CPC .......... C12N 15/79; C12N 1/12; A01G 33/00; C07K 14/80
See application file for complete search history.

(56) References Cited

U.S. PATENT DOCUMENTS 10,087,428 B2 * 10/2018 Ozaki ...................... C12N 9/16
2015/0140592 A1 * 5/2015 Oard .......................... C12P 3/00
435/257.2

FOREIGN PATENT DOCUMENTS

KR          101855739 B1 *  6/2017

OTHER PUBLICATIONS

Leister, D. (2019). Genetic engineering, synthetic biology and the light reactions of photosynthesis. Plant physiology, 179(3), 778-793 (Year: 2018).*
Barrera, D. J., & Mayfield, S. P. (2013). High-value recombinant protein production in microalgae. Richmond A, Emeritus, Hu Q. Handbook of microalgal culture: Applied phycology and biotechnology. 2nd edition. Hoboken: John Wiley & Sons, Ltd, 532-44 (Year: 2013).*
Keun machine translation (Year: 2017).*
De Vree et al., "Comparison of four outdoor pilot-scale photobioreactors," Biotechnology for Biofuels, Dec. 2015, 12 pages.
Kramer et al., "New fluorescence parameters for the determination of QA redox state and excitation energy fluxes," Photosynthesis Research, Feb. 2004, 79(2): 209-218.
Krause et al., "Chlorophyll fluorescence and photosynthesis: The basics," Annual Review of Plant Physiology and Plant Molecular Biology, Jun. 1991, 42:313-349.
Maxwell et al., "Chlorophyll fluorescence—a practical guide," Journal of Experimental Botany, Apr. 2000, 51(345):659-668.

* cited by examiner

*Primary Examiner* — Louise W Humphrey
*Assistant Examiner* — Trevor L Kane
(74) *Attorney, Agent, or Firm* — Fish & Richardson P.C.

(57) ABSTRACT

The present disclosure relates to the fields of biotechnology, molecular biology and genetic engineering. In particular, the present disclosure relates to a genetically modified alga comprising a recombinant cytochrome c6 gene, methods of producing the same and applications thereof. The present disclosure also relates to a codon optimised nucleic acid sequence encoding a cytochrome c6 polypeptide, expression cassette, vectors and host cell thereof. In an embodiment, the present disclosure also relates to a method of increasing biomass and photosynthetic efficiency of algae.

20 Claims, 4 Drawing Sheets

Specification includes a Sequence Listing.

GENETICALLY MODIFIED ALGA, SEQUENCES AND METHODS THEREOF

TECHNICAL FIELD

The present disclosure relates to the fields of biotechnology, molecular biology and genetic engineering. In particular, the present disclosure relates to a genetically modified alga comprising a recombinant cytochrome c6 gene, methods of producing the same and applications thereof. The present disclosure also relates to a codon optimised nucleic acid sequence encoding a cytochrome c6 polypeptide, expression cassette, vectors and host cell thereof. In an embodiment, the present disclosure also relates to a method of increasing biomass and photosynthetic efficiency of algae.

BACKGROUND OF THE DISCLOSURE

Algae biomass is critical for biofuel production and high value products, and improvement and increase in biomass production has always remained a complex and challenging process. Both extrinsic and intrinsic factors govern the process of algae biomass improvement. While many inventions demonstrated improvements in the area of extrinsic factors such as those including cultivation system design, system modifications and changes in cultivation process including photobioreactor design based strategies, overcoming bottlenecks in intrinsic processes within microalgae remained a huge challenge. The process of photosynthesis and electron transfer process is one such rate limiting intrinsic factor towards algae biomass improvement. The photosynthesis process in microalgae is initiated by capture of light or photon, followed by the utilization of the energy of photon and generation of reductants. Furthermore, most of the downstream reactions are carried out by mobile electron carriers or redox carriers in the linear electron transport. In the linear electron transport process many redox reactions and redox molecules determine the overall rate of the reaction. One of the major rate limiting step(s) in the overall process is the redox imbalance in the electron transport chain and re-oxidation of redox carrier plastoquinone. While some literature showed antenna truncation, overexpression of ferredoxin gene at PS I (photosystem I) level, improving RUBISCO enzyme activity or improving rate limiting enzymes of Calvin Benson Bassham cycle improves photosynthesis in algae or enhances heat stress tolerance, none of these modifications increased the biomass productivity in microalgae. Further, additional drawbacks of prior art methods include futile reactions in the photosynthesis process such as photodamage and photoinhibition due to excess light or nutrient limitation in microalgae cultivation.

It is therefore important to overcome these bottlenecks and/or rate limiting step(s) for improving rate of photosynthesis for biomass improvement in algae, since improving biomass productivity will improve the economics of biofuel and other high value algal product(s) such as protein, nutraceuticals, variety of biologicals, etc.

SUMMARY OF THE DISCLOSURE

The present disclosure relates to a genetically modified alga comprising a recombinant cytochrome c6 gene.

The present disclosure also relates to a method of obtaining the said genetically modified alga, comprising acts of:

a) introducing a nucleic acid or vector or expression cassette comprising recombinant cytochrome c6 gene in to an algal cell; and b) selecting modified algal cell expressing the recombinant gene to obtain the genetically modified alga.

The present disclosure also relates to a nucleic acid sequence encoding a cytochrome c6 polypeptide comprising sequence as set forth in SEQ ID. NO. 1 or a variant having at least 80% identity to SEQ ID. NO. 1; a vector comprising the said nucleic acid sequence and an operably linked promoter; an expression cassette comprising nucleic acid sequence encoding a cytochrome c6 polypeptide comprising sequence as set forth in SEQ ID. NO. 1 or a variant having at least 80% identity to SEQ ID. NO. 1, nucleic acid encoding chloroplast targeting peptide sequence and an operably linked promoter; and a host cell comprising the said nucleic acid sequence, vector or expression cassette.

The present disclosure also relates to a method of producing algae biomass by culturing the said genetically modified alga under conducive conditions.

The present disclosure also relates to a method of enhancing production of biomass or photosynthetic efficiency in alga, said method comprising culturing the said genetically modified alga, to achieve enhanced production of biomass or photosynthetic efficiency.

The present disclosure also relates to use of the said genetically modified alga for production of biomass, high value protein, nutraceuticals, biologicals and/or biofuel.

BRIEF DESCRIPTION OF ACCOMPANYING FIGURES

In order that the disclosure may be readily understood and put into practical effect, reference will now be made to exemplary embodiments as illustrated with reference to the accompanying figures. The figures together with detailed description below, are incorporated in and form part of the specification, and serve to further illustrate the embodiments and explain various principles and advantages, in accordance with the present disclosure where:

Figure 3:
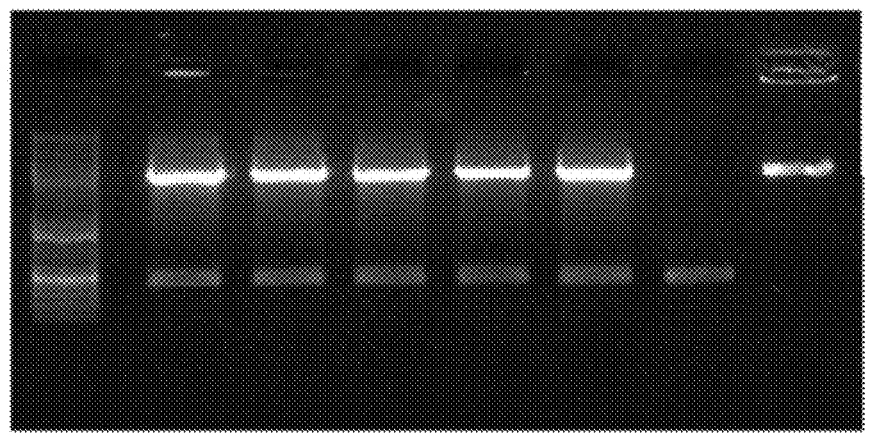

FIG. 3 depicts confirmation of clones with KpnI and XbaI restriction enzyme digestion (lane M=1 kb pair DNA Molecular Weight Marker from Thermo Fisher; lanes 1-5=confirmed clones of Cytochrome C6; lane 6=PCR Product of CytC6 as positive control (432 bp); and lane 7=Empty pChlamy4 vector digested with KpnI and XbaI restriction enzymes).

Figure 4:
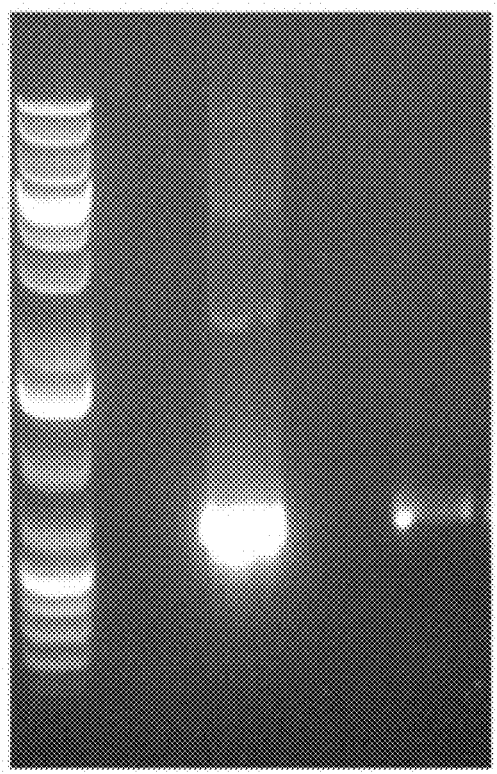

FIG. 4 depicts confirmation of cytochrome c6 transformant in *Chlorella sorokiniana* strain using specific primers (lane M=1 kb pair DNA Molecular Weight Marker, Thermo Fischer; lane 1=No template control; lane 2=Positive control from plasmid; lane 3=Wild type strain genomic DNA PCR; and lane 4=positive cytochrome c6 transformant).

Figure 5:
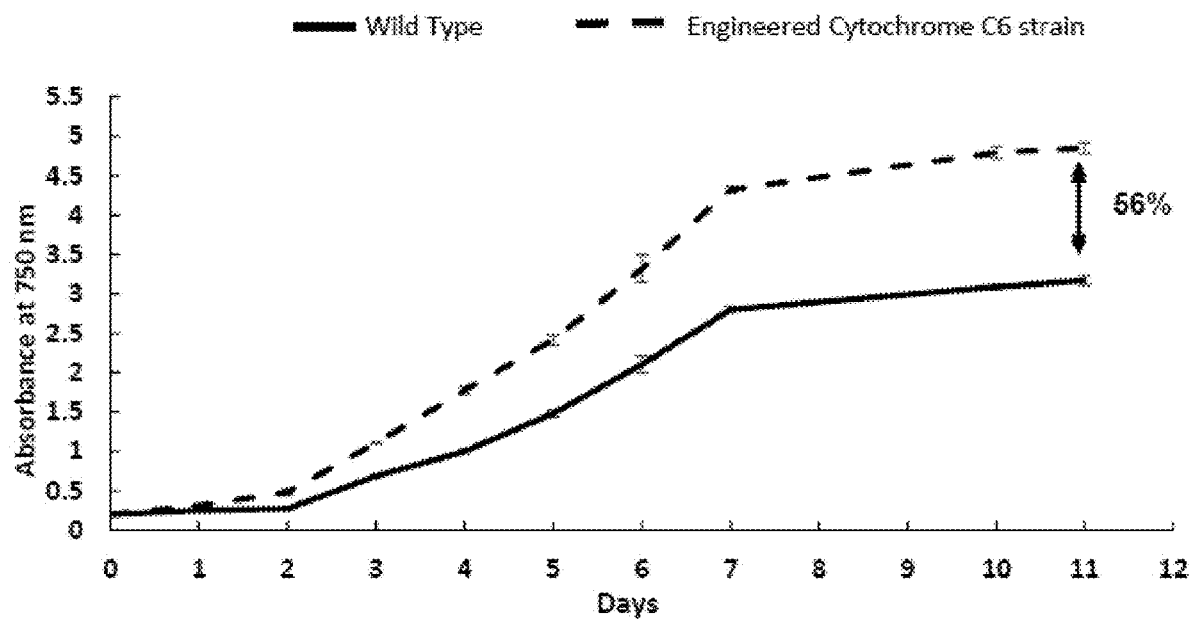

FIG. 5 depicts growth assays under batch mode of cultivation demonstrating 56% growth improvement in cytochrome c6 engineered *Chlorella sorokiniana* strain compared to the wild type strain.

Figure 6:
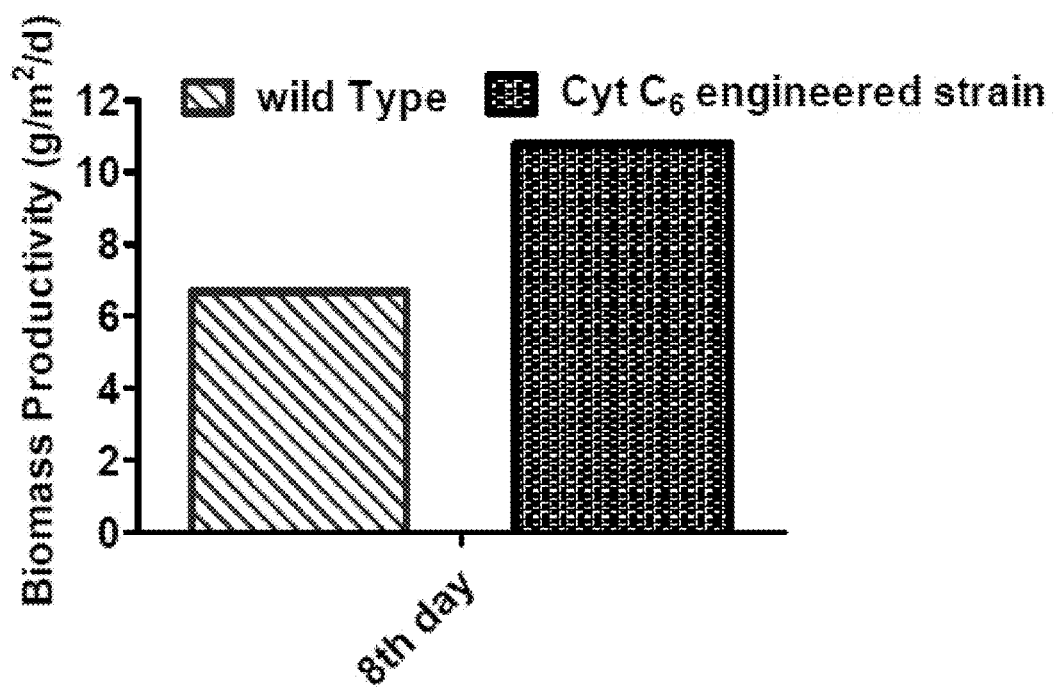

FIG. 6 depicts biomass productivity under fed-batch mode of cultivation in shallow depth of 10 cm demonstrating >60% productivity improvement in cytochrome c6 engineered *Chlorella sorokiniana* strain compared to the wild type strain after 8 days. 4th day was considered as initial time point for productivity calculation.

Figure 7:
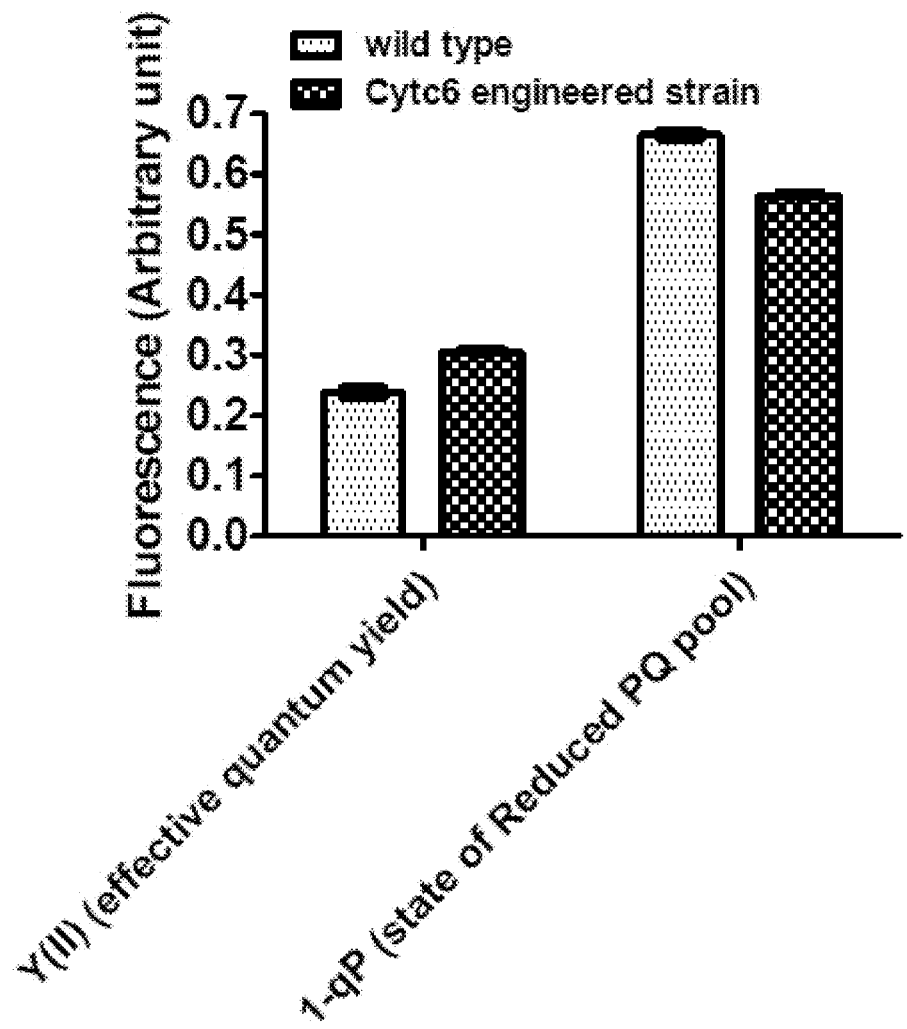

FIG. 7 depicts chlorophyll 'a' fluorescence based photosynthetic performance assessment demonstrating 28% improvement in effective PSII (photosystem II) quantum yield in the case of cytochrome c6 engineered strain in comparison to the wild type strain and >20% improvement in the plastoquinone oxidized pool in cytochrome c6 engineered strain when compared to the wild type strain.

BRIEF DESCRIPTION OF THE ACCOMPANYING SEQUENCE LISTINGS

In order that the disclosure may be readily understood and put into practical effect, reference will now be made to exemplary embodiments as illustrated with reference to description of the sequence listings. The sequences together with detailed description below, are incorporated in and form part of the specification, and serve to further illustrate the embodiments and explain various principles and advantages, in accordance with the present disclosure where:

Sequence Id. No. 1 represents the codon optimized nucleic acid sequence for *Chlorella sorokiniana* of the cytochrome c6 gene obtained from *Porphyra yezoensis*.

Sequence Id. No. 2 represents the nucleic acid sequence encoding a chloroplast targeting signal peptide.

Sequence Id. No. 3 represents the corresponding amino acid sequence of Sequence Id. No. 1.

Sequence Id. No. 4 represents the corresponding amino acid sequence of Sequence Id. No. 2.

Sequence Id. No. 5 represents the native nucleic acid sequence of the cytochrome c6 gene of *Porphyra yezoensis*.

Sequence Id. No. 6 represents the forward primer sequence employed for confirmation of positively cloned expression vector.

Sequence Id. No. 7 represents the reverse primer sequence employed for confirmation of positively cloned expression vector.

Sequence Id. No. 8 represents the vector specific forward primer employed for confirmation of positively transformed microalgae.

Sequence Id. No. 9 represents the gene specific reverse primer employed for confirmation of positively transformed microalgae.

Sequence Id. No. 10 represents the complete nucleic acid sequence of the present disclosure comprising Sequence Id. No. 1 and Sequence Id. No. 2.

Sequence Id. No. 11 represents the corresponding amino acid sequence of Sequence Id. No. 10.

Sequence Id. No. 12 represents the Hsp70A-RBCS2 promoter in pChlamy4.

DETAILED DESCRIPTION

The present disclosure overcomes the various drawbacks of the prior art and provides for efficient means and modes to solve bottlenecks and rate limiting steps of photosynthesis in algae.

However, before describing the process in greater detail, it is important to take note of the common terms and phrases that are employed throughout the instant disclosure for better understanding of the technology provided herein.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The use of the expression "at least" or "at least one" suggests the use of one or more elements or ingredients or quantities, as the use may be in the embodiment of the disclosure to achieve one or more of the desired objects or results. Throughout this specification, the word "comprise", or variations such as "comprises" or "comprising" or "containing" or "has" or "having" wherever used, will be understood to imply the inclusion of a stated element, integer or step, or group of elements, integers or steps, but not the exclusion of any other element, integer or step, or group of elements, integers or steps.

As used herein, the terms "method" and "process" are used interchangeably.

As used herein, the term "about" means to be nearly the same as a referenced number or value. As used herein, the term "about" should be generally understood to encompass ±10% of a specified amount or value.

As used herein, the term "microalgae" refers to microscopic eukaryotic algae generally green in colour due to the presence of chlorophyll a and chlorophyll b, typically found in fresh water, brackish water and marine water systems and exist as unicellular species. Microalgae carry out photosynthesis process by which carbon is fixed in the form of biomass (carbohydrate, protein, lipid) using sunlight, carbon dioxide and water and releasing oxygen into the atmosphere.

As used herein, the terms the "genetically modified algae", "recombinant algae", "recombinant strain", "engineered algae", "engineered strain", "cytochrome c6 recombinant algae/strain" and "cytochrome c6 engineered algae/strain" are used interchangeably in reference to algae comprising an evolutionary distinct cytochrome C6 gene from a different species, such as but not limiting to red algae, having iron metalloprotein redox carrier having a conducive redox potential and capability to improve plastoquinone redox status, more specifically improved plastoquinone oxidized pool which is considered as one of the rate limiting step of photosynthesis.

As used herein, the terms "algae" and "algal cells" are used interchangeably and include but are not limited to microalgae. In a non-limiting embodiment of the present disclosure, the algae is selected from group comprising but not limiting to *Chlorella* sp., *Nannochloropsis* sp., *Nannochloris* sp., *Neochloris* sp., *Pseudoneochloris* sp., *Chlamydomonas* sp and *Picochlorum* sp. In another non-limiting embodiment of the present disclosure, the algae is selected from group comprising but not limiting to cyanobacteria, diatoms, dinoflagellates, *Spirulina* etc.

In preferred embodiments of the present disclosure, the algae is green algae selected from *Chlorella* sp. In an exemplary embodiment, the algae is *Chlorella sorokiniana*.

As used herein, the terms "microalgae" and "microalgal cells" are used interchangeably.

As used herein, the term "green algae" refers to photosynthetic eukaryotes originated following an endosymbiosis event to evolve a membrane bound organelle called chloroplast which contain chlorophyll a and chlorophyll b in stacked thylakoids, providing them bright green colour appearance. They mostly store starch in the chloroplast As used herein, the term "red algae" refers to distinct group of eukaryotic algae, without flagella and centrioles, and chloroplasts that lack external endoplasmic reticulum, contain unstacked thylakoids and use phycobiliproteins as accessory pigments (specially phycoerythrin) which imparts them red colour.

As used herein, the term "recombinant cytochrome c6 gene" is used in reference to the gene sequence of the present disclosure and is intended to mean that the cytochrome c6 gene sequence introduced in the genetically modified alga is chemically synthesized polynucleotide sequence and is not normally found in a naturally occurring strain of the referenced species, including wild-type strains of the referenced species. The recombinant cytochrome c6 gene is accordingly from a different species than the alga which is modified and is codon-optimized for introducing it in said alga. In an embodiment, the cytochrome c6 gene is obtained from red algae. In an exemplary embodiment, the red algae is from *Porphyra* sp. such as *Porphyra yezoensis*.

The present disclosure pertains to a genetically modified alga comprising a recombinant cytochrome c6 gene.

The present disclosure also pertains to a method of obtaining the afore-described genetically modified alga, said method comprising steps of:
a) introducing a nucleic acid or vector or expression cassette comprising recombinant cytochrome c6 gene in to an algal cell; and
b) selecting modified algal cell expressing the recombinant gene to obtain the genetically modified alga.

In embodiments of the present disclosure, the recombinant cytochrome c6 gene employed in the present disclosure is from a different species than the alga which is modified.

In a preferred embodiment of the present disclosure, the said cytochrome c6 gene is obtained from red algae and is codon-optimized for the alga which is to be genetically modified. In an exemplary and non-limiting embodiment of the present disclosure, the red algae is *Porphyra yezoensis*.

In an exemplary embodiment of the present disclosure, the said cytochrome c6 gene is obtained from red algae such as *Porphyra yezoensis* and is codon-optimized for the alga which is to be genetically modified.

In embodiments of the present disclosure, the alga which is to be genetically modified is microalgae, preferably green algae.

In embodiments of the present disclosure, the alga which is to be genetically modified is selected from a group comprising *Chlorella* sp., *Nannochloropsis* sp., *Nannochloris* sp., *Neochloris* sp., *Pseudoneochloris* sp., *Chlamydomonas* sp., *Picochlorum* sp., cyanobacteria, diatoms, dinoflagellates, and *Spirulina* or any combination thereof.

In an exemplary embodiment, the alga which is to be genetically modified is *Chlorella sorokiniana*.

In a non-limiting embodiment of the present disclosure, the recombinant cytochrome c6 gene employed in the present disclosure comprises a nucleotide sequence set forth as SEQ ID NO. 1 or a variant having at least 80% identity to SEQ ID NO. 1, wherein said SEQ ID NO. 1 is codon-optimized for *Chlorella sorokiniana*.

In embodiments of the present disclosure, the cytochrome c6 expressed by the recombinant gene is targeted to thylakoid lumen of chloroplast of the genetically modified algae by a chloroplast targeting peptide.

In a non-limiting embodiment of the present disclosure, the nucleic acid encoding the chloroplast targeting peptide is set forth in SEQ ID. NO. 2 or a variant having at least 80% identity to SEQ ID. NO. 2.

In embodiments of the present disclosure, the recombinant cytochrome c6 gene comprises the nucleic acid sequence as set forth in SEQ ID. NO. 10 or a variant having at least 80% identity to SEQ ID. NO. 10.

In embodiments of the present disclosure, the genetically modified alga comprises an expression cassette comprising a recombinant cytochrome c6 gene encoding a cytochrome c6 polypeptide, nucleic acid encoding chloroplast targeting peptide and an operably linked promoter.

In embodiments of the present disclosure, the genetically modified alga is *Chlorella sorokiniana* having Accession Number CCAP 211/135, received in the Culture Collection of Algae and Protozoa (SAMS Ltd., Scottish Marine Institute, OBAN, Argyll PA37 1QA, UK) on Apr. 24, 2019, and accepted for deposit for patent purposes on May 10, 2019.

In embodiments of the present disclosure, the genetically modified alga of the present disclosure has characteristics selected from a group comprising enhanced production of biomass, enhanced photosynthetic efficiency, resistance to stress or any combination thereof.

In an embodiment, the present disclosure provides for a genetically modified microalga comprising a recombinant cytochrome c6 gene of red algae.

In embodiments of the present disclosure, the genetically modified alga is characterized by having enhanced production of biomass, enhanced photosynthetic efficiency, stress tolerance to high heat and/or high salinity etc, as compared to wild type microalga.

In embodiments of the present disclosure, the method of obtaining the afore-described genetically modified alga comprises acts of:
a) introducing a vector or expression cassette comprising recombinant cytochrome c6 gene derived from red algae in to the algal cells; and
b) growing the algal cells on a medium comprising a selective agent under conducive conditions to facilitate overexpression of said cytochrome C6 to obtain the genetically modified alga.

In embodiments of the present disclosure, the method of obtaining the afore-described genetically modified alga comprises acts of:
a) weakening or removing cell wall of algal cells to prepare algae for gene transfer;
b) introducing a vector or expression cassette comprising recombinant cytochrome c6 gene derived from red algae in to the algal cells; and
c) growing the algal cells on a medium comprising a selective agent under conducive conditions to facilitate overexpression of said cytochrome C6 to obtain the genetically modified alga.

In an embodiment, the method of obtaining the genetically modified microalga comprises a) introducing a nucleic acid or vector or expression cassette comprising recombinant cytochrome c6 gene derived from red algae in to microalgal cell; and b) selecting modified microalgal cell expressing the recombinant gene to obtain the genetically modified microalga.

In an embodiment, the method of obtaining the genetically modified microalgae comprises acts of: a) introducing a vector or expression cassette comprising recombinant cytochrome c6 gene derived from red algae in to microalgal cells; b) expressing the recombinant gene to produce the cytochrome C6; and c) selecting transformed microalgal cells to obtain the genetically modified microalgae.

In an embodiment, the present disclosure pertains to a method of producing a genetically modified microalgae having recombinant cytochrome c6 in the thylakoid lumen of chloroplast, comprising step of introducing a gene encoding a fused protein comprising a signal peptide and a cytochrome c6 protein into the genome of a microalgae, wherein the signal peptide is a chloroplast targeting peptide and wherein the cytochrome c6 gene is from red algae and codon optimised for the microalgae which is to be modified.

In embodiments of the present disclosure, the vector or the expression cassette is introduced in the algal cells which are to be genetically modified by technique selected from a group comprising biolistic, glass beads, carbon whiskers, agrobacterium mediated genetic transformation and electroporation, preferably electroporation.

The selectable agent/marker employed in the present disclosure comprises a resistance agent possessing resistance to at least one compound selected from a group which includes but is not limited to an antibiotic compound and a toxic compound. In a non-limiting embodiment of the present disclosure, the selective agent is selected from a group comprising antibiotic selection marker and toxic compound.

Exemplary and non-limiting examples of suitable antibiotic selection markers that can be used in the present disclosure include ampicillin, carbenicillin, other beta-lactamases, zeocin, bleomycin, hygromycin, tetracyclin and paramomycin.

One of the key rate limiting step is at the cytochrome b6f level and electron transfer between cytochrome b6f and photosystem I. There are two evolutionary related molecules that carry out the function of electron transfer between cytochrome b6f and p700 reaction centre of photosystem I. One is cytochrome c6, a heme iron containing water soluble redox carrier protein and present mostly in cyanobacteria, red algae and some of the green eukaryotic algae but absent in plants. Many green algae and higher plants cytochrome c6 molecule has been replaced by copper containing plastocyanin molecule for electron transfer. The structures of these two electron carrier proteins are different, however they are similar in size and midpoint redox potential, suggesting similar function. In green algae, depending on the presence of metal ions such as iron or copper in the growth media, synthesis of redox carriers such as cytochrome c6 and plastocyanin are regulated. The redox molecules can also be affected by process of oxidative stress during high light or high salt or any such stress conditions or combinations of stress conditions. In the linear electron transport chain of photosynthesis process in algae many rate limiting steps are proposed, including rate at which photons are collected and processed, many futile reactions in the photosynthesis process including photodamage and photoinhibition due to excess light or nutrient limitation in algae cultivation. However, there are very prominent bottlenecks and rate limiting steps in and around cytochrome b6f molecule and rate at which electron or reducing equivalents are delivered at photosystem I level for NADPH generation. Therefore, the present disclosures provide to overcome bottleneck of photosynthesis at cytochrome b6f and PSI level for enhancing biomass productivity in algae/microalgae for commercial sustainability of biofuels and bioproducts from algae/microalgae.

The present disclosure accordingly provides for genetically engineering algae preferably a green microalgae with cytochrome c6 gene preferably from red algae with conducive midpoint redox potential for faster transfer of electrons between cytochrome b6f and photosystem I. Overexpression of cytochrome c6 gene in the chloroplast of the recombinant algae/green microalgae and resultant protein helps in improving effective quantum yield of photosystem II, improving plastoquinone oxidation pool and thereby enhances biomass productivity and photosynthetic efficiency in engineered strain compared to the wild type strain.

In an embodiment of the present disclosure, to improve the rate limiting step of electron transfer between PSII and PSI via cytochrome b6f and overcome the bottleneck of over-reduction of plastoquinone pool, a suitable redox carrier cytochrome c6 gene from red algae such as *Porphyra yezoensis* is genetically transformed into an algae such as but not limiting to *Chlorella* sp. and overexpressed, targeted to chloroplast via a chloroplast targeting peptide. Expressed cytochrome c6 protein is a water soluble thylakoid lumen protein and redox carrier of electrons. Due to its conducive midpoint electric potential and unique structure providing resistance to auto-oxidation it will help in faster electron transfer from cytochrome b6f to photosystem I. Due to its structural uniqueness in providing protection against oxidation, this redox molecule will help during stress conditions such as high light, high salinity, and/or combinations of such conditions etc. and will improve electron transfer process. Faster electron transfer will aid in faster NADPH and ATP generation, which in turn will improve Calvin Benson Bassham cycle carbon fixation activity and will result in biomass improvement.

In embodiments of the present disclosure, the unique structure of the Cyt6 of red algae employed in the present disclosure confers additional advantages. The red algae cytochrome c6 has unique structure in terms of amino acid stretch and functional attributes which provides resistance to auto-oxidation or prevent damage from oxidation process. No other known cytc6 protein has such unique structure that contributes to functional aspects of resistance to photodamage.

In general, some green algae including some of the *Chlorella* sp. have endogenous cytochrome c6 along with plastocyanin. However, the engineered strain of the present disclosure comprising the recombinant Cyt6 of red algae has improved biomass productivity compared to the wild-type strain.

In embodiments of the present disclosure, the recombinant Cyt6 of red algae confers resistance to oxidative damage at high light, high salinity or different stress conditions.

The present disclosure relates to a codon optimised nucleic acid sequence encoding a cytochrome c6 polypeptide.

In embodiments of the present disclosure, the cytochrome c6 gene sequence is codon optimized prior to expression in algae such as but not limiting to *Chlorella*. This is done by taking native cytochrome c6 gene from red algae, preferably *Porphyra yezoensis*, as a template to prepare the codon optimized version for expression in microalgae of the present disclosure, for example *Chlorella sorokiniana*. The codon optimized version of the cytochrome c6 gene (set forth as Sequence Id. No. 1) is accordingly chemically synthesized.

In embodiments of the present disclosure, the nucleic acid sequence encoding cytochrome c6 polypeptide comprises Sequence Id. No. 1 or a variant thereof having at least 80% identity to Sequence Id. No. 1.

In a preferred embodiment, the nucleic acid sequence encoding a cytochrome c6 polypeptide is as set forth in Sequence Id. No. 1 or a variant thereof having at least 80% identity to Sequence Id. No. 1.

In embodiments of the present disclosure, the nucleic acid sequence encoding cytochrome c6 polypeptide comprises Sequence Id. No. 1 or a variant thereof having at least 85% identity to Sequence Id. No. 1.

In embodiments of the present disclosure, the nucleic acid sequence encoding cytochrome c6 polypeptide comprises Sequence Id. No. 1 or a variant thereof having at least 90% identity to Sequence Id. No. 1.

In embodiments of the present disclosure, the nucleic acid sequence encoding cytochrome c6 polypeptide comprises Sequence Id. No. 1 or a variant thereof having at least 95% identity to Sequence Id. No. 1.

In embodiments of the present disclosure, the nucleic acid sequence encoding cytochrome c6 polypeptide comprises Sequence Id. No. 1 or a variant thereof having at least 99% identity to Sequence Id. No. 1.

In an exemplary embodiment, the nucleic acid sequence encoding a cytochrome c6 polypeptide is as set forth in Sequence Id. No. 1.

In an embodiment, the nucleic acid sequence of the present disclosure encodes an amino acid sequence as set forth in Sequence Id. No. 3 or a variant thereof having at least 80% identity to Sequence Id. No. 3.

In an exemplary embodiment, the nucleic acid sequence as set forth in Sequence Id. No. 1 encodes a cytochrome c6 polypeptide as set forth in Sequence Id. No. 3.

The present disclosure also relates to a codon optimised nucleic acid sequence encoding a chloroplast targeting peptide (CTP). Any CTP sequence that aids in targeting the cytochrome C6 protein into the chloroplast can be employed in the present disclosure.

In embodiments of the present disclosure, the nucleic acid sequence encoding a chloroplast targeting peptide comprises Sequence Id. No. 2 or a variant thereof having at least 80% identity to Sequence Id. No. 2.

In an exemplary embodiment, the nucleic acid sequence as set forth in Sequence Id. No. 2 encodes a chloroplast targeting peptide as set forth in Sequence Id. No. 4.

In an exemplary and non-limiting embodiment of the present disclosure, the nucleic acid sequence encoding a chloroplast targeting peptide or the chloroplast targeting peptide is Violaxanthin/Chlorophyll a binding protein (VCP) from *Nannochloropsis* sp.

In embodiments of the present disclosure, a nucleic acid encoding the chloroplast targeting peptide (set forth as Sequence Id. No. 2) is added at the N-terminal end of the cytochrome c6 gene sequence.

Thus, in a preferred embodiment, the codon optimized version of the cytochrome c6 gene (set forth as Sequence Id. No. 1) along with a N-terminal nucleic acid encoding the chloroplast targeting peptide (set forth as Sequence Id. No. 2) is chemically synthesized. The codon optimized version of the nucleic acid encoding the cytochrome c6 polypeptide along with the nucleic acid encoding the N-terminal chloroplast targeting peptide is set forth as Sequence Id. No. 10.

The present disclosure also relates to an expression cassette comprising codon optimised nucleic acid sequence encoding a cytochrome c6 polypeptide, nucleic acid encoding chloroplast targeting peptide sequence and an operably linked promoter.

In an embodiment, the expression cassette comprises nucleic acid sequence encoding a cytochrome c6 polypeptide comprising sequence as set forth in SEQ ID. NO. 1 or a variant having at least 80% identity to SEQ ID. NO. 1, nucleic acid encoding chloroplast targeting peptide sequence and an operably linked promoter.

In an embodiment, the expression cassette comprises the nucleic acid sequence as set forth in Sequence Id. No. 1 or a variant thereof having at least 80% identity to Sequence Id. No. 1, nucleic acid encoding chloroplast targeting peptide sequence as set forth in Sequence Id. No. 2 or a variant thereof having at least 80% identity to Sequence Id. No. 2 and an operably linked promoter.

In an embodiment, the nucleic acid sequence as set forth in Sequence Id. No. 2 encodes a chloroplast targeting peptide sequence as set forth in Sequence Id. No. 4.

In an exemplary embodiment, the expression cassette comprises the nucleic acid sequence as set forth in Sequence Id. No. 10 or variants thereof and an operably linked promoter.

In a non-limiting embodiment, the present disclosure relates to *Chlorella sorokiniana* codon optimized polynucleotide sequence of red algae *Porphyra* cytochrome c6 gene along with suitable promoter and nucleotide sequence encoding for chloroplast targeting peptide in green microalgae.

The present disclosure also relates to a vector comprising the nucleic acid sequence or expression cassette of the present disclosure as described above.

In an embodiment, the said vector comprises the nucleic acid sequence or expression cassette comprising Sequence Id. No. 1 or a variant thereof having at least 80% identity to Sequence Id. No. 1.

In an embodiment, the said vector comprises the nucleic acid sequence encoding cytochrome c6 polypeptide comprises Sequence Id. No. 1 or a variant thereof having at least 80% identity to Sequence Id. No. 1 operably linked to a promoter.

In an embodiment, the vector comprises the expression cassette comprising the nucleic acid sequence as set forth in Sequence Id. No. 1 or a variant thereof having at least 80% identity to Sequence Id. No. 1, nucleic acid encoding chloroplast targeting peptide sequence as set forth in Sequence Id. No. 2 or a variant thereof having at least 80% identity to Sequence Id. No. 2 and an operably linked promoter.

In an embodiment, the vector further comprises selection markers such as antibiotic selection markers and one or more restriction enzyme digestion site.

The vector of the present disclosure includes cloning vector and expression vector.

In embodiments of the present disclosure, any constitutive promoter which works in microalgae such as but not limiting to green algae can be employed in the present disclosure.

In an exemplary embodiment, the promoter of the afore-described vector or expression cassette comprises sequence as set forth in SEQ ID. NO. 12.

The present disclosure also relates to a host cell comprising any of the afore-described nucleic acid sequence, vector or expression cassette. of the present disclosure.

In non-limiting embodiments of the present disclosure, the host cell could be selected from bacterial or algal cell. In an embodiment, the host cell is algae, preferably microalgae.

In exemplary embodiments of the present disclosure, the host cell is selected from a group comprising *Escherichia* sp., *Chlorella* sp., *Nannochloropsis* sp., *Nannochloris* sp., *Neochloris* sp., *Pseudoneochloris* sp., *Chlamydomonas* sp., *Picochlorum* sp. or any combination thereof.

In exemplary embodiments of the present disclosure, the host cell is selected from a group comprising cyanobacteria, diatoms, dinoflagellates and *Spirulina* or any combination thereof.

In embodiments of the present disclosure, the microalgae is green algae.

The present disclosure also relates to a method of producing recombinant algae with a recombinant cytochrome c6 gene from red algae, and the recombinant algae obtained thereof.

In an embodiment of the present disclosure, the method of producing recombinant algae comprises acts of:
a) preparing a vector comprising a recombinant nucleic acid encoding a cytochrome c6 polypeptide,
b) transforming algal cell(s) with said vector; and
c) selecting transformed algal cell(s) to obtain the recombinant algae.

In an embodiment of the present disclosure, the method of producing recombinant algae comprises acts of:
a) preparing an expression vector comprising the nucleic acid sequence encoding cytochrome c6 polypeptide comprising Sequence Id. No. 1 or a variant thereof having at least 80% identity to Sequence Id. No. 1,
b) transforming algal cell(s) with said expression vector; and
c) selecting transformed algal cell(s) to obtain the recombinant algae.

In an embodiment of the present disclosure, the method of producing recombinant algae comprises acts of:
a) preparing an expression vector comprising the nucleic acid sequence encoding cytochrome c6 polypeptide comprising Sequence Id. No. 1 or a variant thereof having at least 80% identity to Sequence Id. No. 1 operably linked to a promoter,
b) transforming algal cell(s) with said expression vector; and
c) selecting transformed algal cell(s) to obtain the recombinant algae.

In an embodiment of the present disclosure, the method of producing recombinant algae comprises acts of:
a) preparing an expression vector comprising the nucleic acid sequence as set forth in Sequence Id. No. 1 or a variant thereof having at least 80% identity to Sequence Id. No. 1, nucleic acid encoding chloroplast targeting peptide sequence as set forth in Sequence Id. No. 2 or a variant thereof having at least 80% identity to Sequence Id. No. 2 and an operably linked promoter,
b) transforming algal cell(s) with said expression vector; and
c) selecting transformed algal cell(s) to obtain the recombinant algae.

In an embodiment of the present disclosure, the method of producing recombinant algae comprises acts of:
a) preparing an expression vector comprising the nucleic acid sequence as set forth in Sequence Id. No. 10 or variants thereof and an operably linked promoter,
b) transforming algal cell(s) with said expression vector; and
c) selecting transformed algal cell(s) to obtain the recombinant algae.

In non-limiting embodiments of the present disclosure, the promoter employed in the vector or expression vector of the present disclosure is as set forth in Sequence Id. No. 12 or a variant thereof.

In embodiments of the present disclosure, the algal cell is selected from the genus *Chlorella, Nannochloropsis, Nannochloris, Neochloris, Peudoneochloris, Chlamydomonas*, and *Picochlorum*. In an exemplary embodiment, the algal cell is *Chlorella sorokiniana*.

In embodiments of the present disclosure, the algal cell is selected from group comprising but not limiting to cyanobacteria, diatoms, *Spirulina* etc.

In embodiments of the present disclosure, the Sequence Id. No. 10 is cloned into a vector, preferably an expression vector, selected from a group comprising but not limiting to pChlamy1, pChlamy3, pChlamy4, etc., preferably pChlamy4 expression vector, using specific restriction sites. In a non-limiting embodiment, the restriction sites are KpnI and XBaI/BglII. Once cloned, positive clones are confirmed by polymerase chain reaction (PCR) using suitable primers and restriction enzyme digestion.

Any suitable primer can be employed for carrying out the PCR reactions in the present disclosure. In a non-limiting embodiment, the primers employed for carrying out the PCR is set forth as Sequence Id. Nos. 6 and 7. In another non-limiting embodiment, the restriction enzyme digestion is carried out using a pair of restriction enzymes KpnI and XBaI/BglII.

In embodiments of the present disclosure, the vector, preferably pChlamy 4, along with ampicillin and zeocin antibiotic selection markers, also comprises suitable constitutive promoter sequence of hsp70A-rbcS2, which along with the N-terminal chloroplast targeting peptide sequence helps in carrying the expressed protein into the chloroplast thylakoid lumen of *Chlorella* strain.

In embodiments of the present disclosure, the resulting vectors are transformed into *Escherichia coli* for confirming the expression and isolating the plasmid (pChlamy4/cytc6) for further transformation into *Chlorella*. Since the expression vector preferably comprises an antibiotic selection marker, positive clones are identified using the antibiotic containing media for growth of the cells. In a non-limiting embodiment, the antibiotic employed for selection is ampicillin or zeocin or both.

In embodiments of the present disclosure, the resulting vector comprising the codon optimized nucleic acid encoding the cytochrome c6 polypeptide along with the nucleic acid encoding the N-terminal chloroplast targeting peptide (Sequence Id. No. 10) is employed to transform the microalgae employed in the present disclosure, preferably *Chlorella sorokiniana*. In a preferred embodiment, an exponentially grown culture of *Chlorella sorokiniana* is employed for the said transformation.

In embodiments of the present disclosure, the vector comprising the codon optimized sequence of the present disclosure is linearized with restriction enzyme for transformation of the microalgae. In a non-limiting embodiment, the vector is linearized with a PvuI restriction enzyme. The resultant linearized DNA is electroporated at a field strength of about 500-1500 V/cm, resistance of about 800Ω and capacitance of about 50 µF. In an exemplary embodiment, the electroporation is carried out in about 0.2 cm cuvettes with about 2-5 µg of linearized DNA in using GENEART® MAX EFFICIENCY® transformation protocol.

In embodiments of the present disclosure, selection of transformed algal cell(s) to obtain the recombinant algae is carried out by screening the cells on a suitable medium containing suitable antibiotic and markers.

In embodiments of the present disclosure, selection of transformed algal cell(s) to obtain the recombinant algae is carried out by screening on suitable media such as but not limiting to copper depletion media, high iron containing media, etc.

In exemplary embodiment of the present disclosure, the algal cells are cultured on medium selected from a group comprising but not limiting to 1% Tris-acetate-phosphate (TAP) agar, Urea phosphoric acid media, Nitrate containing F/2 media, BG11 media with Nitrate, etc, or combinations thereof.

In embodiments of the present disclosure, upon electroporation, the transformed cells are plated in a suitable medium containing the antibiotic, a marker for which is provided in the desired transformant. In a non-limiting embodiment, the medium is selected from a group comprising 1% Tris-acetate-phosphate (TAP) agar, Urea phosphoric acid media, Nitrate containing F/2 media, BG11 media with Nitrate, etc. The plates are incubated in very low light with equal light/dark cycle at room temperature. In a non-limiting embodiment, the light employed for the incubation is of about 30 to about 50 µmoles/m2/s photon flux density with 12:12 light/dark cycle and at temperature of about 23° C. to about 24° C. Colony formation is observed and genomic DNA is isolated from engineered microalgae, preferably *Chlorella sorokiniana*, as well as wild type strain. Positive clone is confirmed by PCR using a combination of specific primers. In a non-limiting embodiment, the combination of primers is a combination of vector specific forward primer set forth in Sequence Id. No. 8 and gene specific reverse primer set forth in Sequence Id. No. 9.

In an embodiment, once cytochrome c6 protein is expressed and targeted to chloroplast, it helps for accepting electron from Cytochrome b6f complex and donate the electron to p700 reaction centre of photosystem I.

The present disclosure also relates to recombinant algae comprising the recombinant nucleotide sequence/expression cassette/vector of the present disclosure. The recombinant algae of the present disclosure comprises a recombinant cytochrome c6 gene from red algae.

In an embodiment, the present disclosure provides for improvement in algae biomass production even in outdoor environment simulation conditions. The algae and methods of the present disclosure have better plastoquinone oxidation and thereby improved redox conditions, which in turn improved biomass productivity in high light and high salinity conditions.

In an embodiment, the recombinant algae, preferably microalgae and more preferably green microalgae comprises an evolutionary distinct gene from red algae preferably from *Porphyra yezoensis* having iron metalloprotein redox carrier having a conducing redox potential and capability to improve plastoquinone redox status, more specifically improved plastoquinone oxidized pool which is considered as one of the rate limiting step of photosynthesis.

In another embodiment, the recombinant algae comprises nucleic acid sequence encoding cytochrome c6 polypeptide comprising sequence as set forth in Sequence Id. No. 1 or a variant thereof.

In another embodiment, the recombinant algae comprises nucleic acid sequence encoding cytochrome c6 polypeptide comprising sequence as set forth in Sequence Id. No. 1 or a variant thereof having at least 80% identity to Sequence Id. No. 1.

In another embodiment, the recombinant algae comprises nucleic acid sequence as set forth in Sequence Id. No. 1 or a variant thereof having at least 80% identity to Sequence Id. No. 1, nucleic acid encoding chloroplast targeting peptide sequence as set forth in Sequence Id. No. 2 or a variant thereof having at least 80% identity to Sequence Id. No. 2 and an operably linked promoter.

In another embodiment, the recombinant algae comprises an expression vector comprising the nucleic acid sequence as set forth in Sequence Id. No. 10 or a variant thereof and an operably linked promoter. In an embodiment, the vector is in the linearized form in the recombinant algae.

The recombinant algae preferably microalgae with cytochrome c6 gene from red algae with conducive midpoint redox potential allows for faster transfer of electrons between cytochrome b6f and photosystem I.

In embodiments of the present disclosure, the recombinant algae strain demonstrates at least 10%, preferably at least 20% and more preferably at least 60% improvement in photosynthetic efficiency under outdoor light and temperature mimicking conditions, as well as at least 10%, preferably at least 20% and more preferably at least 60% improved biomass which is economically suitable for growing the recombinant strain outdoor commercial cultivation system in a shallow pond or PBR which will have low fresh water requirement The present disclosure also relates to a method of producing algae biomass by culturing the cytochrome c6 recombinant algae of the present disclosure under ambient/conducive conditions.

The present disclosure also relates to a method of enhancing production of biomass in alga, said method comprising culturing the afore-described genetically modified alga to achieve enhanced production of algae biomass.

In an embodiment, the present disclosure pertains to a method of promoting growth of a genetically modified microalgae, comprising acts of:
introducing a gene encoding a fused protein comprising a signal peptide and a cytochrome c6 protein into the genome of a microalgae; and
expressing the gene under suitable conditions;
wherein the cytochrome c6 is located in the thylakoid space of chloroplast,
wherein the signal peptide is a chloroplast targeting peptide and wherein the cytochrome c6 gene is from red algae and codon optimised for the microalgae which is to be modified.

In embodiments of the present disclosure, the method for producing algae biomass comprises acts of:
a) culturing cytochrome c6 recombinant algae of the present disclosure in a suitable culture medium under conditions permitting the growth/photosynthesis of the algal cells for production of biomass,
b) optionally recovering said algae biomass from the culture medium, and
c) optionally purifying the recovered biomass.

In embodiments of the present disclosure, the method for producing algae biomass comprises acts of:
a) culturing cytochrome c6 recombinant algae of the present disclosure in a suitable culture medium under conditions permitting the growth/photosynthesis of the algal cells for production of biomass such as temperature, light, shaking, aeration, etc.,
b) optionally recovering said algae biomass from the culture medium, and
c) optionally purifying the recovered biomass.

In embodiments of the present disclosure, the recombinant algae of the present disclosure are cultured on culture medium selected from a group comprising but not limiting to Tris-acetate phosphate media, Urea phosphoric acid media, F2N2 media with Nitrate and BG11 media with nitrate or combinations thereof. In embodiments of the present disclosure, the culturing is carried out at a temperature ranging from about 25-35° C. In embodiments of the present disclosure, the recombinant algae culture is subjected to light of about 200-2000 $\mu$moles/m$^2$/s of photon flux density, shaking of about 100-400 rpm, with aeration, with 2-5% $CO_2$ and air mix, with/without vitamins.

In embodiments of the present disclosure, the method for producing algae biomass comprises acts of:
a) culturing cytochrome c6 recombinant algae of the present disclosure in a suitable culture medium for production of biomass at a temperature ranging from about 25-35° C. and light of about 200-2000 $\mu$moles/m$^2$/s of photon flux density, optionally shaking the culture at about 100-400 rpm, optionally with about 2-5% $CO_2$ and air mix, optionally along with vitamins,
b) optionally recovering said algae biomass from the culture medium, and
c) optionally purifying the recovered biomass.

In an embodiment, the method comprises overexpressing the cytochrome c6 gene in the chloroplast of the recombinant algae preferably green microalgae and resultant protein helps in improving effective quantum yield of photosystem II, improving plastoquinone oxidation pool, allowing faster transfer of electrons between cytochrome b6f and photosystem I and thereby enhancing biomass productivity and photosynthetic efficiency by more than 20% in the recombinant strain compared to the wild type strain. In an embodiment, the recombinant strain when evaluated in shallow depth in environmental photobioreactor in fed batch mode, demonstrated 20% improvement in biomass productivity under simulating outdoor conditions. Therefore, the recombinant algae provides commercial importance for biomass improvement in outdoor cultivation system for the production of biofuel and high value bio-products.

The present disclosure also relates to the method for increasing the photosynthetic efficiency of algae.

In embodiments of the present disclosure, the method for increasing the photosynthetic efficiency of algae comprises act of culturing the afore-described genetically modified alga to achieve enhanced photosynthetic efficiency.

In embodiments of the present disclosure, the method for increasing the photosynthetic efficiency of algae comprises acts of:
a) preparing an expression vector comprising the nucleic acid sequence encoding cytochrome c6 polypeptide comprises sequence set forth in Sequence Id. No. 1 or a variant thereof having at least 80% identity to Sequence Id. No. 1,
b) transforming algal cell(s) with said expression vector;
c) selecting transformed algal cell(s) to obtain the recombinant algae,
d) culturing cytochrome c6 recombinant algae of the present disclosure in a suitable culture medium under conditions permitting photosynthesis of the algae.

In embodiments of the present disclosure, the method for increasing the photosynthetic efficiency of algae comprises acts of:
a) preparing an expression vector comprising the nucleic acid comprising sequence set forth in Sequence Id. No. 10 or a variant thereof having at least 80% identity to Sequence Id. No. 10 operably linked to a promoter,
b) transforming algal cell(s) with said expression vector;
c) selecting transformed algal cell(s) to obtain the recombinant algae,
d) culturing recombinant algae of the present disclosure in a suitable culture medium under conditions permitting photosynthesis of the algae.

In embodiments of the present disclosure, the genetically modified alga achieves enhanced biomass production or photosynthetic efficiency relative to corresponding wild-type alga.

In embodiments of the present disclosure, the methods or conducive conditions of the present disclosure comprise culturing the genetically modified alga at a temperature ranging from about 25° C. to about 35° C. and for a time-period ranging from about 24 hours to about 300 hours.

In embodiments of the present disclosure, the methods or conducive conditions of the present disclosure comprise culturing the genetically modified alga under light of about 200-2000 µmoles/m$^2$/s of photon flux density.

In embodiments of the present disclosure, the methods or conducive conditions of the present disclosure comprise culturing the genetically modified alga in about 2-5% $CO_2$ and air mix.

In embodiments of the present disclosure, the algae biomass obtained from the methods of the present disclosure is recovered from culture medium and optionally purified by conventional techniques.

In embodiments of the present disclosure, culturing of the cytochrome c6 recombinant algae preferably microalgae, and more preferably green microalgae such as *Chlorella sorokiniana* is carried out in batch mode or fed-batch mode of cultivation.

In embodiments of the present disclosure, growth assay of cytochrome c6 recombinant algae preferably microalgae, and more preferably green microalgae such as *Chlorella sorokiniana* and wild type strains is carried out in batch mode of cultivation. In a non-limiting embodiment, for the growth assay, the engineered and wild type microalgae, including *Chlorella*, are grown at about 4% sea water salinity, on urea phosphoric acid media at a temperature of about 25-35° C., in a Kuhner shaker at about 50-400 rpm rotation. $CO_2$ concentration is maintained at about 2-5%, while humidity is at about 50-70%. The photon flux density is of about 200-2000 µmoles/m$^2$/s with light and dark cycles (L:D) of about 12:12-16:8 h, preferably about 12:12 h or 14:10 h or 16:8 h L:D cycle, including but not limiting to fast light dark cycle of millisecond to second range and flashing light dark cycle of high frequency light on and off state.

In embodiments of the present disclosure, the cytochrome c6 engineered microalgae demonstrates at least 50% growth improvement when compared with the wild type strain.

In embodiments of the present disclosure, growth assay of cytochrome c6 engineered algae, such as *Chlorella sorokiniana* and wild type strains is carried out in fed-batch mode of cultivation. In a non-limiting embodiment, the fed-batch mode of cultivation is carried out in shallow depth (such as but not limiting to 5-15 cm), corresponding to outdoor mimicking conditions. In an exemplary embodiment, for the growth assay, the engineered and wild type algae are grown at about 2-5% sea water salinity, on urea phosphoric acid media at a temperature ranging between about 25° C. to about 35° C., at about 100-500 rpm rotation. $CO_2$ concentration is maintained at about 1-5%, while the photon flux density is of about 200-2000 µmoles/m2/s with light and dark cycles with 10 cm of culture depth, wherein the light is calibrated at about 10 cm culture surface preferably using LI-COR® PAR quantum sensor. In an embodiment, the light and dark cycles is of about 12:12-16:8 h, preferably about 12:12 h or 14:10 h or 16:8 h L:D cycle, including but not limiting to fast light dark cycle of millisecond to second range and flashing light dark cycle of high frequency light on and off state.

In embodiments of the present disclosure, the cytochrome c6 engineered algae demonstrates at least 20%, preferably at least 50% more preferably at least 60% improvement in productivity when compared with the wild type strain.

In embodiments of the present disclosure, assessment of photosynthetic efficiency of the cytochrome c6 engineered algae and wild type strains is calculated based on the following equations (modified from de Vree et al; 2015):

> Energy output from the product/Energy input from the light=Biomass productivity (g/m$^2$/d)×Standard enthalpy of combustion (KJ/g)/daily aerial photon flux density (mols/m$^2$/d)×Energetic content of white LED PAR light (kJ/mol).

In an embodiment, % Photosynthetic efficiency is calculated by the formula: Energy output from biomass÷Energy input from white LED light×100.

In embodiments of the present disclosure, the cytochrome c6 engineered algae demonstrates at least 20% increase in photosynthetic efficiency when compared with the wild type strain.

In embodiments of the present disclosure, assessment of photosynthetic performance of cytochrome c6 engineered algae and wild type strains is carried out by studying the chlorophyll 'a' fluorescence parameters. In a non-limiting embodiment, the parameters are monitored using a pulse amplitude modulated fluorimeter (Dual-Pam-100, Heinz Walz, Effeltrich, Germany). For this assessment, in exemplary embodiments, the algal cells are initially kept in darkness for about 10 minutes, post which the cells are illuminated with a red measuring beam (at about 655 nm) to determine minimal fluorescence ($F_o$) using a measuring light of about 0.24 μmol photons m$^{-2}$ s$^{-1}$. Thereafter, about 400 ms saturation pulse (of about 10000 μmol photons m$^2$ s$^{-1}$) is used to determine the maximal fluorescence yield ($F_m$). Dark adapted values for $F_m$ and $F_o$ are measured on cells placed in darkness minimum for about 10 minutes so as to obtain maximal quantum yield of PSII, $F_v/F_m$, $F_v=F_m-F_o$, (Krause & Weis 1991). Induction kinetics are performed using red actinic light (of about 1000 μmol photons m$^2$ s$^{-1}$). The quantum yields of photochemical quenching, Y(II) and closure of PSII reaction centres (1−qP) are calculated from the fluorescence obtained after actinic light is switched on, to estimate the partitioning of light energy as follows:

$$Y(II)=(Fm'-F)/Fm'\text{(Maxwell et al., 2000)}$$

$$1-qP=1-[(F'm-Ft)/(F'm-F'o)]\text{(Kramer et al., 2004)}$$

In embodiments of the present disclosure, the cytochrome c6 engineered algae demonstrates at least 20% increase in light adapted effective yield [Y(II)] when compared with the wild type strain.

In further embodiments of the present disclosure, the cytochrome c6 engineered algae demonstrates at least 20% increase in improvement of the plastoquinone oxidation pool when compared with the wild type strain.

In further embodiments of the present disclosure, the cytochrome c6 engineered algae demonstrates increased photosynthetic performance by at least 20%, resulting in increased biomass productivity when compared with the wild type strain.

In an embodiment of the present disclosure, cloning and overexpression of codon optimized red algae *Porphyra yezoensis* cytochrome c6 gene into the chloroplast of *Chlorella* strain improves the PSII effective quantum yield and improves the oxidized pool of plastoquinone, which in turn improves the photosynthetic efficiency by at least 10%, preferably at least 20% and more preferably at least 60% and this resulted in improvement of biomass productivity in engineered strain of *Chlorella* by at least 60% compared to the wild type strain.

In an embodiment, the chlorophyll a fluorescence data demonstrates at least 20% improvement in the plastoquinone (PQ) oxidized pool. Increased oxidized PQ pool leads to the better redox equilibrium in the linear electron transport chain and might positively influence many rate limiting enzymes of light reaction as well as rate liming enzymes of Calvin cycle. Hence, improvement in the PQ redox through engineering codon optimized cytochrome c6 gene helps in faster electron extraction from cytochrome b6f providing conducive photosystem I chemistry and thereby helping faster NADPH generation. Overall photosynthesis improvement definitely mediates faster carbon fixation and enhanced biomass in the engineered strain.

In an embodiment, cytochrome c6 is expressed normally under presence of copper in the media, however using the approach of constitutive expression using hsp70A-rbcS2 promoter, it is possible to overexpress this protein in conditions where copper is absent in the media. This is one of the key advantages of the method, where in strains having only plastocyanin as a redox carrier of the electron and due to the limitation of copper in the media, electron transfer will be highly impacted due to inhibition of synthesis of plastocyanin and eventually it will slow down the carbon fixation and biomass production. The recombinant algae will continue to carry electrons and produce enhance biomass even under copper limiting conditions in the media and inside the cell.

In an exemplary and non-limiting embodiment of the present disclosure, a codon optimized DNA sequence for *Chlorella sorokiniana* was used as starting polynucleotide sequence using red algae *Porphyra yezoensis* cytochrome c6 DNA sequence as the template. The codon optimized 432 base pair polynucleotide sequence of cytochrome c6 was cloned into an expression vector known as pChlamy 4. The cytochrome c6 gene was cloned in between KpnI and BglII restriction enzyme sites. Positive clones were confirmed by polymerase chain reaction (PCR) using appropriate primer sequences and restriction enzyme digestion using pair of restriction enzyme KpnI and XBaI. The resultant plasmid of pChlamy4 along with cloned cytochrome c6 gene was used as starting material for genetic transformation in *Chlorella sorokiniana* strain. pChlamy 4 has a suitable constitutive promoter sequence of hsp70A-rbcS2, with ampicillin and zeocin as antibiotic selection markers and was used along with an N-terminal chloroplast targeting peptide sequence for carrying the expressed protein into the chloroplast thylakoid lumen of *Chlorella* strain. For genetic transformation of pChlamy4/cytc6 plasmid, exponentially grown culture of *Chlorella sorokiniana* was taken. pChlamy4/cytc6 plasmid was linearized with PvuI restriction enzyme and then resultant DNA was electroporated under following conditions: Field strength—about 500V/cm; Resistance—800Ω; and Capacitance—50 μF. After electroporation, transformed cells were plated in 1% Tris-acetate-phosphate agar plates containing zeocin antibiotic selection marker. The positive genetic transformant was confirmed by isolation of genomic DNA and PCR using specific primer sets. Cytochrome c6 protein is expressed and targeted to chloroplast, and helps for accepting electron from Cytochrome b6f complex and donate the electron to p700 reaction centre of photosystem I. When the engineered strain was evaluated in kuhner shaker for growth in batch mode, it showed about 56% improved growth compared to the wild-type strain. Further growth evaluation in fed batch mode in shallow depth of about 5-15 cm using about 1000 μmoles/m2/s of sinusoidal light mimicking outdoor light, temperature, humidity and $CO_2$ conditions, engineered strain showed at least 20% improvement in photosynthetic efficiency and in turn resulted in at least 20% improvement in biomass productivity on ash free dry weight basis. To decipher the increase in the photosynthesis efficiency in the cytochrome c6 engineered strain, both wild type and engineered strains were characterized such as by chlorophyll a fluorescence kinetics analyses using Dual PAM 100 fluorimeter under growth light conditions. In the cytochrome c6 engineered strain, light adapted effective quantum yield, Y (II) was found to be increased by about 28% compared to the wild type strain under growth light conditions of about 500 μmoles/m$^2$/s photon flux density. Engineered cytochrome c6 strain demonstrated improvement in the plastoquinone oxidation pool compared to the wild type strain, indicating cytochrome c6 engineering improves photosynthesis and biomass in *Chlorella sorokiniana* strain. Methionine residues in cytochrome c6 protein act as endogenous protectant for oxidation under stress conditions.

The present disclosure also relates to use of the aforedescribed genetically modified alga for production of biomass.

The present disclosure also relates to use of the afore-described genetically modified alga for production of high value protein. As used herein, "high value protein" refers to microalgae derived proteins having complete profile of essential amino acids (such as Leucine. Lysine, Phenylalanine, tryptophan etc.), high protein content (e.g more than 45-50% of cell dry weight) and/or in combinations with antioxidant molecules/pigments having high economic value.

The present disclosure also relates to use of the afore-described genetically modified alga for production of biofuel.

The present disclosure also relates to use of the afore-described genetically modified alga for production of nutraceuticals.

The present disclosure also relates to use of the afore-described genetically modified alga for production of biologicals.

In embodiments of the present disclosure, the advantages of the present disclosure include but are not limited to the following:

Provides for stable genetic modification for biomass improvement in algae/microalgae which is an economic solution for industrial process.

The present disclosure overcomes the rate liming and bottleneck step via better redox poise of plastoquinone pool and improving the oxidation of plastoquinone in algae will help in faster electron transfer from photosystem II to photosystem I via cytochrome b6f. This in turn helps in faster NADPH pool and Calvin cycle activity for biomass enhancement. In an embodiment, recombinant algae of the present disclosure results in improvement in oxidized pool of engineered *Chlorella* strain by at least 20% under high light (such as but not limiting to of about 1000 $\mu moles/m^2/s$) and/or high salinity compared to the wild type.

Improved biomass productivity and photosynthetic efficiency of the recombinant algae improves the economics of biofuel and algae high value product economics. In an embodiment, recombinant algae of the present disclosure results in improvement of biomass productivity in engineered strain by at least 20% under high light of 1000 $\mu moles/m^2/s$ and high salinity in shallow depth compared to the wild type.

The growth of the recombinant strain of the present disclosure under high $CO_2$ atmosphere (about 2-5% of $CO_2$) renders the present disclosure environmentally important to reduce $CO_2$ induced climate change.

The overall photosynthetic efficiency and biomass growth improvement of the recombinant strain of the present disclosure is superior and ideal for outdoor conditions with salinity stress.

Improved biomass strain through genetic engineering require less capital expenditures (CAPEX) and operating expenses (OPEX) as compared to new cultivation system design or modification.

The recombinant algae of the present disclosure works in shallow depth, hence it could be used in shallow raceway pond, as well as in photobioreactor (PBR) system with narrow path length producing greater degree of freedom in cultivation system operation. In an embodiment, recombinant algae of the present disclosure results in improvement of photosynthetic efficiency in engineered strain by at least 20% preferably by at least 60% grown under fed batch condition in shallow depth compared to the wild type.

Cytochrome c6 engineering approach could be adapted in C3 plants for crop photosynthesis improvement and thereby aerial productivity in agriculture sector.

In an embodiment, recombinant algae of the present disclosure (expressing codon optimized red algae cytochrome c6 gene) results in improvement in photosystem II effective quantum yield by more than 20%.

The recombinant algae of the present disclosure can be grown commercially even under copper limiting condition which will provide economic advantage. It also acts as a water soluble carrier of electrons from cytochrome b6f molecule to p700 reaction centre of the photosystem I.

Due to unique structure of this cytochrome c6 protein, it provides protection against oxidation during stress conditions like high light, high salinity or combination of both.

The exemplary recombinant algae strain of the present disclosure was deposited with Culture Collection of Algae and Protozoa (CCAP), SAMS Ltd., Scottish Marine Institute, OBAN, Argyll PA37 1QA, UK, on Apr. 24, 2019, was accepted for deposit for patent purposes on May 10, 2019, and has been accorded the accession number CCAP 211/135 *Chlorella sorokiniana* OE C6.

Additional embodiments and features of the present disclosure will be apparent to one of ordinary skill in art based on the description provided herein. The embodiments herein provide various features and advantageous details thereof in the description. Descriptions of well-known/conventional methods and techniques are omitted so as to not unnecessarily obscure the embodiments herein.

Any possible combination of two or more of the embodiments described herein is comprised within the scope of the present disclosure.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments in this disclosure have been described in terms of preferred embodiments, those skilled in the art will recognize that the embodiments herein can be practiced with modification within the spirit and scope of the embodiments as described herein.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

Further, while the instant disclosure is susceptible to various modifications and alternative forms, specific aspects thereof has been shown by way of examples and drawings and are described in detail below. However, it should be understood that it is not intended to limit the invention to the particular forms disclosed, but on the contrary, the intention is to cover all modifications, equivalents, and alternatives falling within the spirit and the scope of the invention.

EXAMPLES

The present disclosure is further described with reference to the following examples, which are only illustrative in nature and should not be construed to limit the scope of the present disclosure in any manner.

Example 1: Preparation of Gene Sequence Prior to Expression in Chlorella

Native cytochrome c6 gene from *Porphyra yezoensis* was used as a template to prepare the codon optimized version for expression in *Chlorella sorokiniana*. The codon optimized version of the cytochrome c6 gene (set forth as Sequence Id. No. 1) was chemically synthesized and a nucleic acid encoding chloroplast targeting peptide was added as a pre-sequence (set forth as Sequence Id. No. 2). The corresponding amino acid sequences are set forth in Sequence Id. Nos. 3 and Sequence Id. No. 4, respectively. The native cytochrome c6 gene from *Porphyra yezoensis* is set forth in Sequence Id. No. 5. (bold and italics part)

Figure 1:
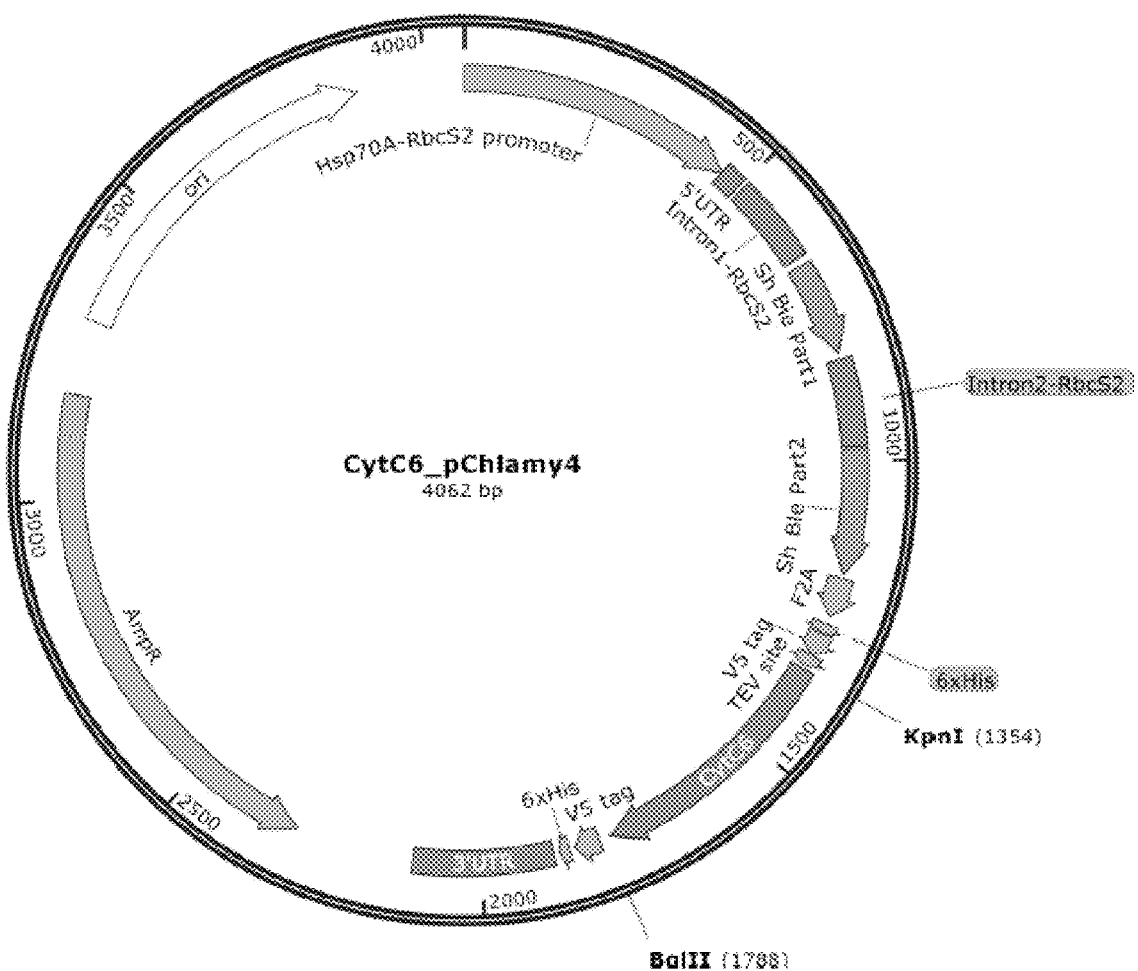
FIG. 1 depicts cytochrome c6_pChlamy4 circular plasmid map construct (4062 base pairs) having promoter element and antibiotic selection markers.
Figure 2:
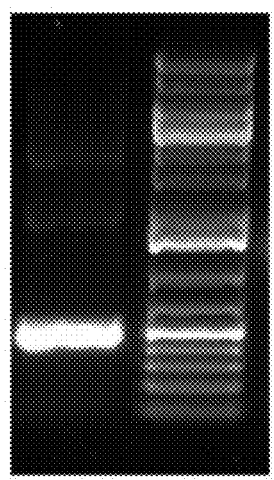
FIG. 2 depicts PCR amplification of cytochrome c6 gene (lane 1=Cytochrome C6 gene product of 432 base pairs; and lane 2=1 kilo base pair DNA Molecular Weight Marker, Thermo Fisher).

The codon optimized 432 base pair polynucleotide sequence (including 99 base pairs of the pre-sequence) of cytochrome c6 was cloned into pChlamy 4 expression vector using the restriction sites KpnI and BglII (FIG. 1). The said codon optimised polynucleotide sequence including the nucleic acid encoding the chloroplast targeting peptide is set forth as Sequence Id. No. 10 and the corresponding amino acid sequence is set forth in Sequence Id. No. 11. Positive clones were confirmed by polymerase chain reaction (PCR) using primers set for as Sequence Id. Nos. 6 and 7 (FIG. 2); followed by restriction enzyme digestion using pair of restriction enzymes KpnI and XbaI (FIG. 3).

The resulting vectors were transformed into *Escherichia coli* (BL21 cells from THERMOFISHER SCIENTIFIC®) for confirming the expression and isolating the plasmid (pChlamy4/cytc6) for transformation into *Chlorella*. Since the expression vector comprises ampicillin/zeocin antibiotic selection marker, positive clones were identified using the 100 µg/ml of ampicillin for growth of the cells.

Example 2: Genetic Transformation of *Chlorella* with the Codon Optimized Cytochrome c6 Gene The resulting pChlamy 4 plasmid obtained in example 1 was used as the starting material for transforming of *Chlorella sorokiniana* strain (Gagva, Jamnagar, Gujarat). As mentioned previously, the pChlamy 4 along with ampicillin and zeocin antibiotic selection markers, also comprises suitable constitutive promoter sequence of hsp70A-rbcS2 (Sequence Id. No. 12), which along with the N-terminal chloroplast targeting peptide sequence helps in carrying the expressed protein into the chloroplast thylakoid lumen of *Chlorella* strain.

For genetic transformation of pChlamy4/cytc6 plasmid, exponentially grown culture of *Chlorella sorokiniana* was taken. pChlamy4/cytc6 plasmid was linearized with PvuI restriction enzyme and the resultant linearized DNA was electroporated under following conditions:
Field strength—500V/cm
Resistance—800Ω
Capacitance—50 µF Electroporation was carried out in 0.2 cm cuvettes with 2 µg of linearized DNA using GENEART® MAX EFFICIENCY® transformation protocol.

After electroporation, transformed cells were plated in 1% Tris-acetate-phosphate (TAP) agar plates containing zeocin antibiotic selection marker. 2 µg/ml of zeocin was employed as antibiotic selection marker and the plates were incubated in very low light of about 30 to about 50 µmoles/m$^2$/s photon flux density under 12:12 light dark cycle and at room temperature of about 23° C. to about 24° C.

Colony formation was observed and genomic DNA was isolated from engineered *Chlorella sorokiniana* strain as well as wild type strain. Positive clone was confirmed by PCR (FIG. 4) using a combination of vector specific forward primer set forth in Sequence Id. No. 8 (5'-GAAGCAGACCCTGAACTTCG-3') and gene specific reverse primer set forth in Sequence Id. No. 9 (5'-TTAGATCTTTACCAGCCCTTCTCGG-3').

Example 3: Growth Assay of Cytochrome c6 Engineered *Chlorella sorokiniana* and Wild Type Strains in Batch Mode of Cultivation Cytochrome c6 engineered *Chlorella sorokiniana* of the present disclosure (as obtained at the end of example 2 above) was evaluated for its growth characteristics under batch mode of cultivation. For said assessment, the engineered and wild type *Chlorella* were grown at 4% sea water salinity, on urea phosphoric acid media at 25° C. temperature, in a Kuhner shaker at 100 rpm rotation. $CO_2$ concentration was maintained at 2%, while humidity was at 70%. The photon flux density was 350 µmoles/m$^2$/s of 12:12 h of light and dark cycles.

The said growth assays demonstrated 56% growth improvement in cytochrome c6 engineered *Chlorella sorokiniana* strain compared to the wild type strain (FIG. 5).

Example 4: Biomass Productivity Assessment of Cytochrome c6 Engineered *Chlorella sorokiniana* and Wild Type Strains in Fed-Batch Mode of Cultivation Cytochrome c6 engineered *Chlorella sorokiniana* of the present disclosure (as obtained at the end of example 2 above) was evaluated for its growth characteristics including biomass production under fed-batch mode of cultivation in shallow depth of 10 cm (which correspond to outdoor mimicking conditions). For said assessment, the engineered and wild type *Chlorella* were grown at 4% sea water salinity, on urea phosphoric acid media at temperatures ranging between about 25° C. to about 35° C., at 400 rpm rotation. $CO_2$ concentration was maintained at 2%, while the photon flux density was 1000 µmoles/m$^2$/s of 12:12 h of light and dark cycles with 10 cm of culture depth. Light was calibrated at 10 cm culture surface using LI-COR® PAR quantum sensor.

The said biomass productivity assay demonstrated more than 60% productivity improvement in cytochrome c6 engineered *Chlorella sorokiniana* strain compared to the wild type strain after 8 days (FIG. 6).

Example 5: Assessment of Photosynthetic Efficiency

Photosynthetic efficiency was calculated based on the following equations:

% Photosynthetic efficiency=Energy output from biomass÷Energy input from white LED light× 100

Step 1—

Calculation of Energy output from biomass=Aerial productivity (g/m²/d)×Standard enthalpy of biomass combustion(=22.5 kJ/g)

Table 1 provides for calculation of Aerial productivity of wild type and cytochrome c6 engineered strain (recombinant algae of the present disclosure).

TABLE 1

| Wild type strain | Cytochrome c6 engineered strain |
|---|---|
| 1. From ash free dry weight based biomass estimation for *Cholrella sorokiniana* strain. It was found, 1 OD = 250 mg/L For fed batch productivity calculations, difference in biomass was taken between 8$^{th}$ day of growth and 4$^{th}$ day of growth. 4$^{th}$ day was chosen as initial time point, as algae adaptation and acclimation takes around 2-3 days. Environmental photobioreactors (ePBRs) were used for growth evaluation, Biomass volumetric Productivity = (OD of 8$^{th}$ day − OD of 4$^{th}$ day) × 250 mg/L ÷ (Final day − Initial day) For the reactor, volumetric productivity = 70 mg/L/d | 1. From ash free dry weight based biomass estimation for *Cholrella sorokiniana* strain. It was found, 1 OD = 250 mg/L For fed batch productivity calculations, difference in biomass was taken between 8$^{th}$ day of growth and 4$^{th}$ day of growth. 4$^{th}$ day was chosen as initial time point, as algae adaptation and acclimation takes around 2-3 days. ePBRs were used for growth evaluation, Biomass volumetric Productivity = (OD of 8$^{th}$ day − OD of 4$^{th}$ day) × 250 mg/L ÷ (Final day − Initial day) For the reactor, volumetric productivity = 113 mg/L/d |
| 2. Conversion of volumetric productivity to aerial productivity-Illuminated area of ePBR for 10 cm depth = 0.0022 m² Volume of culture = 210 ml = 0.210 L Aerial productivity (in g/m²/d) = (Vol. productivity ÷ 1000) × (0.210 L ÷ 0.0022 m²) (to convert mg to g, its divided by 1000) Aerial productivity in the reactor = 6.68 g/m²/d. | 2. Conversion of volumetric productivity to aerial productivity- Illuminated area of ePBR for 10 cm depth = 0.0022 m² Volume of culture = 210 ml = 0.210 L Aerial productivity (in g/m²/d) = (Vol. productivity ÷ 1000) × (0.210 L ÷ 0.0022 m²) (to convert mg to g, its divided by 1000) Aerial productivity in the reactor = 10.78 g/m²/d. |

Hence, Energy output from wild type strain biomass=6.68 g/m²/d×22.5 kJ/g=150.3 kJ/m²/d.

Energy output from cytc6 engineered strain biomass=10.78 g/m²/d×22.5 kJ/g=242.55 kJ/m²/d.

Step 2—

Calculation of Energy input from the LED Light impinged on the culture=Average photon flux density for 12 h of day light (mol/m²/d)×Energetic content of white LED light Photon flux density was measured with LI-COR®-250 PAR quantum sensor (LI-COR®, USA) in μmol/m²/s.

Average photon flux density for sinusoidal light profile for 12 h/day duration=500 μmol/m²/s, with peak light photon flux density of 1000 μmol/m²/s.

Energetic content of white LED light used=219 kJ/mol.

So, energy input from light=500 μmol/m²/s×3600 (for s to h conversion)×12 h×10$^{-6}$ (for μmol to mol conversion)×219 kJ/mol=4730 kJ/m²/d.

Step 3—

% Photosynthetic efficiency (PE)=Energy output from biomass÷Energy input from white LED light×100.

For, wild type strain, % PE=150.3 kJ/m²/d÷4730 kJ/m²/d×100=3.17%.

For, cytc6 engineered strain, % PE=242.55 kJ/m²/d÷4730 kJ/m²/d×100=5.13%.

Hence, % increase in photosynthetic efficiency in engineered strain is about 61.8%.

Example 6: Assessment of Photosynthetic Performance

Photosynthetic performance was assessed by studying the chlorophyll 'a' fluorescence parameters, which were monitored using a pulse amplitude modulated fluorimeter (Dual-Pam-100, Heinz Walz, Effeltrich, Germany). For all the measurements, cells were kept in darkness for 10 min before fluorescence analysis. The sample illumination with a red measuring beam (at 655 nm) to determine minimal fluorescence (F0) was performed using a measuring light (0.24 μmol photons m$^{-2}$ s$^{-1}$). A 400 ms saturation pulse (10000 μmol photons m$^{-2}$ s$^{-1}$) was used to determine the maximal fluorescence yield ($F_m$). Dark adapted values for $F_m$ and $F_o$ were measured on cells placed in darkness minimum for 10 min so as to obtain maximal quantum yield of PSII, $F_v/F_m$, $F_v=F_m-F_o$, (Krause & Weis 1991). Induction kinetics were performed using red actinic light (1000 μmol photons m$^{-2}$ s$^{-1}$). The quantum yields of photochemical quenching, Y(II) and closure of PSII reaction centres (1−qP) were calculated from the fluorescence obtained after actinic light was switched on, to estimate the partitioning of light energy as follows:

$Y(II)=(Fm'-F)/Fm'$ (Maxwell et al., 2000)

$1-qP=1-[(F'm-Ft)/('Fm-F'o)]$ 1 (Kramer et al., 2004)

Light adapted effective yield [Y(II)] was found to increase by 28% in engineered *Chlorella*, indicating that they exhibit greater heat dissipation capacity over wild type algae. The decreased 1−qP fraction of the engineered reflects the decreased excitation pressure of the redox carriers (plastoquinone pool), probably indicating that the plastoquinone pool is more oxidized (at least 20% improvement) in the engineered *Chlorella* than the wild type (FIG. 7). This demonstrates that overexpressing red alga cytochrome c6 having structural uniqueness of preventing oxidation in green microalgae improves photosynthetic performance by more than 60% and hence, resulted in higher biomass productivity in the engineered *Chlorella* strain.

REFERENCES

1) Kate Maxwell, Giles N. Johnson; Chlorophyll fluorescence—a practical guide, Journal of Experimental Botany, Volume 51, Issue 345, 1 Apr. 2000, Pages 659-668

2) David Kramer, Giles Johnson, Olavi Kiirats and Gerald Edwards; New fluorescence parameters for the determination of QA redox state and excitation energy fluxes, Photosynthesis research 79: 209-218, 2004.

We claim:

1. A genetically modified alga comprising a recombinant cytochrome c6 gene comprising nucleotide sequence set forth as SEQ ID NO. 1 or a variant having at least 80% identity to SEQ ID NO. 1.

2. The genetically modified alga of claim 1, wherein the recombinant cytochrome c6 gene is from a different species than the alga which is modified; wherein the genetically modified alga comprises a chloroplast targeting peptide for targeting cytochrome c6 expressed by the recombinant gene to thylakoid lumen of chloroplast of the genetically modified algae.

3. The genetically modified alga of claim 1, wherein the cytochrome c6 gene is obtained from red algae and is codon-optimized for said modified alga; wherein the red algae is *Porphyra yezoensis*; and wherein the genetically modified alga is selected from the group consisting of *Chlorella* sp., *Nannochloropsis* sp., *Nannochloris* sp., *Neochloris* sp., *Pseudoneochloris* sp., *Chlamydomonas* sp., *Picochlorum* sp., cyanobacteria, diatoms, *Spirulina*, and any combination thereof.

4. The genetically modified alga of claim 1, wherein the alga is *Chlorella sorokiniana*; wherein said SEQ ID NO. 1 is codon-optimized for *Chlorella sorokiniana*; or wherein the genetically modified alga is *Chlorella sorokiniana* having Accession Number CCAP 211/135.

5. The genetically modified alga of claim 2, wherein nucleic acid encoding the chloroplast targeting peptide is set forth in SEQ ID. NO. 2 or a variant having at least 80% identity to SEQ ID. NO. 2; and wherein the genetically modified alga has characteristics selected from the group consisting of enhanced production of biomass, enhanced photosynthetic efficiency, resistance to stress, and any combination thereof.

6. A method of obtaining the genetically modified alga of claim 1, comprising steps of:
   a) introducing a nucleic acid, a vector, or an expression cassette comprising recombinant cytochrome c6 gene comprising the nucleotide sequence set forth as SEQ ID NO. 1 or a variant having at least 80% identity to SEQ ID NO. 1 into an algal cell; and
   b) selecting modified algal cell expressing the recombinant gene to obtain the genetically modified alga.

7. The method of claim 6, wherein the recombinant cytochrome c6 gene is from a different species than the genetically modified alga; wherein the nucleic acid, vector, or the expression cassette is introduced in the algal cells by a technique selected from the group consisting of: biolistic, glass bead, carbon whiskers, *agrobacterium* mediated genetic transformation, and electroporation; and wherein the cytochrome c6 expressed by the recombinant gene is targeted to thylakoid lumen of chloroplast of the genetically modified algae by a chloroplast targeting peptide.

8. The method of claim 6, wherein the cytochrome c6 gene is obtained from red algae and is codon-optimized for said genetically modified alga, wherein the red algae is *Porphyra yezoensis*; and wherein the modified alga is selected from the group consisting of: *Chlorella* sp., *Nannochloropsis* sp., *Nannochloris* sp., *Neochloris* sp., *Pseudoneochloris* sp., *Chlamydomoas* sp., *Picochlorum* sp., cyanobacteria, diatoms, and *Spirulina*, and any combination thereof.

9. The method of claim 6, wherein the modified alga is *Chlorella sorokiniana*; wherein the recombinant cytochrome c6 gene comprises a nucleotide sequence set forth as SEQ ID NO. 1 or a variant having at least 80% identity to SEQ ID NO. 1, wherein said SEQ ID NO. 1 is codon-optimized for *Chlorella sorokiniana* having Accession Number CCAP 211/135.

10. The method of claim 7, wherein nucleic acid encoding the chloroplast targeting peptide is set forth in SEQ ID. NO. 2, or a variant having at least 80% identity to SEQ ID. NO. 2; wherein the genetically modified alga comprises an expression cassette comprising a recombinant cytochrome c6 gene encoding a cytochrome c6 polypeptide, nucleic acid encoding chloroplast targeting peptide, and an operably linked promoter; and wherein the genetically modified alga has characteristics selected from the group consisting of: enhanced production of biomass, enhanced photosynthetic efficiency, resistance to stress and any combination thereof.

11. A nucleic acid sequence encoding a cytochrome c6 polypeptide comprising sequence as set forth in SEQ ID. NO. 1 or a variant having at least 80% identity to SEQ ID. NO. 1.

12. A vector comprising the nucleic acid sequence of claim 11 and an operably linked promoter.

13. An expression cassette comprising the nucleic acid sequence of claim 11, nucleic acid encoding chloroplast targeting peptide sequence and an operably linked promoter.

14. The expression cassette of claim 13, wherein sequence of the nucleic acid encoding chloroplast targeting peptide comprises sequence as set forth in SEQ ID. NO. 2 or a variant thereof having at least 80% identity to SEQ ID. NO. 2; and wherein the promoter comprises sequence as set forth in SEQ ID. NO. 12.

15. A host cell comprising the nucleic acid sequence of claim 11.

16. The host cell of claim 15, wherein the host cell is selected from the group consisting of *Escherichia* sp., *Chlorella* sp., *Nannochloropsis* sp., *Nannochloris* sp., *Neochloris* sp., *Pseudoneochloris* sp., *Chlamydomonas* sp., *Picochlorum* sp., cyanobacteria, diatoms, dinoflagellates, *Spirulina*, and any combination thereof.

17. A method of producing algae biomass by culturing the genetically modified alga of claim 1 under conducive condition.

18. A method of enhancing production of biomass or photosynthetic efficiency in alga, said method comprising culturing the genetically modified alga of claim 1 to achieve enhanced production of biomass or photosynthetic efficiency.

19. The method of claim 18, wherein the method comprises culturing the genetically modified alga at a temperature ranging from about 25° C. to about 35° C. and for a time-period ranging from about 24 hours to about 300 hours; wherein the method optionally comprises culturing the genetically modified alga under light of about 200-2000 µmoles/m$^2$/s of photon flux density, and optionally with about 2-5% CO2 and air mix; optionally recovering the algae biomass, and optionally purifying the recovered algae biomass; and wherein the genetically modified alga achieves enhanced biomass production or photosynthetic efficiency relative to corresponding wild-type alga.

20. A method of using the genetically modified alga of claim 1 for production of biomass, high value protein, nutraceuticals, biologicals or biofuel, comprising step of culturing the genetically modified alga under conducive condition.

* * * * *

SEQUENCE LISTING

<160> NUMBER OF SEQ ID NOS: 12

<210> SEQ ID NO 1
<211> LENGTH: 333
<212> TYPE: DNA
<213> ORGANISM: Artificial Sequence
<220> FEATURE:
<223> OTHER INFORMATION: Codon Optimized Gene Sequence

<400> SEQUENCE: 1

```
atgaagaaaa agctctccgt gctcttcacc gtgttctcct tctttgtgat cggcttcgcc      60
cagatcgcct tcgccgcgga cctcgacaac ggcgagaagg tgttctccgc caactgcgcc     120
gcgtgccacg ccggcggtaa caacgccatc atgcccgaca agaccctcaa aaaggacgtg     180
ctcgaggcca actccatgaa caccatcgac gccatcacct accaggtgca gaacggcaag     240
aacgccatgc ccgccttcgg cggccgcctc gtggacgagg acatcgagga cgctgccaac     300
tacgtgctct cccagtccga gaagggctgg taa                                  333
```

<210> SEQ ID NO 2
<211> LENGTH: 99
<212> TYPE: DNA
<213> ORGANISM: Artificial Sequence
<220> FEATURE:
<223> OTHER INFORMATION: Chloroplast Targeting Signal Peptide

<400> SEQUENCE: 2

```
atgaagaccg ccgcgctctt gaccgtgtcc accctcatgg gcgcccaggc cttcatggcc      60
cccgccccca agttctcccg cacccgcggc gtggcccgc                             99
```

<210> SEQ ID NO 3
<211> LENGTH: 110
<212> TYPE: PRT
<213> ORGANISM: Artificial Sequence
<220> FEATURE:
<223> OTHER INFORMATION: Amino Acid Sequence of the Codon Optimized
      Gene Sequence

<400> SEQUENCE: 3

```
Met Lys Lys Lys Leu Ser Val Leu Phe Thr Val Phe Ser Phe Phe Val
1               5                   10                  15

Ile Gly Phe Ala Gln Ile Ala Phe Ala Ala Asp Leu Asp Asn Gly Glu
            20                  25                  30

Lys Val Phe Ser Ala Asn Cys Ala Ala Cys His Ala Gly Gly Asn Asn
        35                  40                  45

Ala Ile Met Pro Asp Lys Thr Leu Lys Lys Asp Val Leu Glu Ala Asn
    50                  55                  60

Ser Met Asn Thr Ile Asp Ala Ile Thr Tyr Gln Val Gln Asn Gly Lys
65                  70                  75                  80

Asn Ala Met Pro Ala Phe Gly Gly Arg Leu Val Asp Glu Asp Ile Glu
                85                  90                  95

Asp Ala Ala Asn Tyr Val Leu Ser Gln Ser Glu Lys Gly Trp
                100                 105                 110
```

<210> SEQ ID NO 4
<211> LENGTH: 33
<212> TYPE: PRT
<213> ORGANISM: Artificial Sequence
<220> FEATURE:

<223> OTHER INFORMATION: Chloroplast Targeting Signal Peptide

<400> SEQUENCE: 4

Met Lys Thr Ala Ala Leu Leu Thr Val Ser Thr Leu Met Gly Ala Gln
1               5                   10                  15

Ala Phe Met Ala Pro Ala Pro Lys Phe Ser Arg Thr Arg Gly Val Ala
            20                  25                  30

Arg

<210> SEQ ID NO 5
<211> LENGTH: 333
<212> TYPE: DNA
<213> ORGANISM: Porphyra yezoensis

<400> SEQUENCE: 5

```
ttgaagaaga agctttcagt tcttttcact gttttagtt tttttgtaat aggtttcgca    60
caaattgctt tgctgcaga tctagataat ggagaaaaag ttttttctgc taattgtgca   120
gcatgtcatg ctggcggtaa taacgccatt atgccagata aaaccttaaa aaagatgta   180
cttgaagcta atagtatgaa tactattgat gctattactt atcaagtaca aatggtaaa   240
aatgccatgc ctgctttcgg aggtagactg gttgatgaag atattgaaga tgcagcaaat   300
tatgtattat ctcaatctga aaaaggttgg taa                                333
```

<210> SEQ ID NO 6
<211> LENGTH: 23
<212> TYPE: DNA
<213> ORGANISM: Artificial Sequence
<220> FEATURE:
<223> OTHER INFORMATION: Forward Primer

<400> SEQUENCE: 6
aaggtaccat gaagaccgcc gcg                                            23

<210> SEQ ID NO 7
<211> LENGTH: 25
<212> TYPE: DNA
<213> ORGANISM: Artificial Sequence
<220> FEATURE:
<223> OTHER INFORMATION: Reverse Primer

<400> SEQUENCE: 7
ttagatcttt accagccctt ctcgg                                          25

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gaagcagacc ctgaacttcg                                                20

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
ttagatcttt accagccctt ctcgg                                          25

<210> SEQ ID NO 10
<211> LENGTH: 432
<212> TYPE: DNA
<213> ORGANISM: Artificial Sequence
<220> FEATURE:
<223> OTHER INFORMATION: Codon optimised polynucleotide sequence
including the nucleic acid encoding the chloroplast targeting
signal peptide

<400> SEQUENCE: 10

```
atgaagaccg ccgcgctctt gaccgtgtcc accctcatgg gcgcccaggc cttcatggcc      60
cccgccccca agttctcccg cacccgcggc gtggcccgca tgaagaaaaa gctctccgtg     120
ctcttcaccg tgttctcctt ctttgtgatc ggcttcgccc agatcgcctt cgccgcggac     180
ctcgacaacg gcgagaaggt gttctccgcc aactgcgccg cgtgccacgc cggcggtaac     240
aacgccatca tgcccgacaa gaccctcaaa aaggacgtgc tcgaggccaa ctccatgaac     300
accatcgacg ccatcaccta ccaggtgcag aacggcaaga acgccatgcc cgccttcggc     360
ggccgcctcg tggacgagga catcgaggac gctgccaact acgtgctctc ccagtccgag     420
aagggctggt aa                                                         432
```

<210> SEQ ID NO 11
<211> LENGTH: 143
<212> TYPE: PRT
<213> ORGANISM: Artificial Sequence
<220> FEATURE:
<223> OTHER INFORMATION: Amino Acid Sequence of the Codon Optimized
Gene Sequence including the Chloroplast Targeting Signal Peptide

<400> SEQUENCE: 11

```
Met Lys Thr Ala Ala Leu Leu Thr Val Ser Thr Leu Met Gly Ala Gln
1               5                   10                  15

Ala Phe Met Ala Pro Ala Pro Lys Phe Ser Arg Thr Arg Gly Val Ala
            20                  25                  30

Arg Met Lys Lys Lys Leu Ser Val Leu Phe Thr Val Phe Ser Phe Phe
        35                  40                  45

Val Ile Gly Phe Ala Gln Ile Ala Phe Ala Ala Asp Leu Asp Asn Gly
    50                  55                  60

Glu Lys Val Phe Ser Ala Asn Cys Ala Ala Cys His Ala Gly Gly Asn
65                  70                  75                  80

Asn Ala Ile Met Pro Asp Lys Thr Leu Lys Lys Asp Val Leu Glu Ala
                85                  90                  95

Asn Ser Met Asn Thr Ile Asp Ala Ile Thr Tyr Gln Val Gln Asn Gly
            100                 105                 110

Lys Asn Ala Met Pro Ala Phe Gly Gly Arg Leu Val Asp Glu Asp Ile
        115                 120                 125

Glu Asp Ala Ala Asn Tyr Val Leu Ser Gln Ser Glu Lys Gly Trp
    130                 135                 140
```

<210> SEQ ID NO 12
<211> LENGTH: 461
<212> TYPE: DNA
<213> ORGANISM: Artificial Sequence
<220> FEATURE:
<223> OTHER INFORMATION: Hsp70A-RbcS2 promoter in pChlamy4

<400> SEQUENCE: 12

```
tcgctgaggc ttgacatgat tggtgcgtat gtttgtatga agctacagga ctgatttggc      60
```

-continued

```
gggctatgag ggcgggggaa gctctggaag ggccgcgatg gggcgcgcgg cgtccagaag    120
gcgccatacg gcccgctggc ggcacccatc cggtataaaa gcccgcgacc ccgaacggtg    180
acctccactt tcagcgacaa acgagcactt atacatacgc gactattctg ccgctataca    240
taaccactca gctagcttaa gatcccatca agcttgcatg ccgggcgcgc cagaaggagc    300
gcagccaaac caggatgatg tttgatgggg tatttgagca cttgcaaccc ttatccggaa    360
gccccctggc ccacaaaggc taggcgccaa tgcaagcagt tcgcatgcag ccccctggagc   420 ggtgccctcc tgataaaccg gccaggggc ctatgttctt t                         461
```